(12) United States Patent
Stefanski et al.

(10) Patent No.: US 11,992,658 B2
(45) Date of Patent: *May 28, 2024

(54) INJECTION DEVICE FOR DELIVERING A DEFINED NUMBER OF EQUAL DOSES OF A FLUID SUBSTANCE

(71) Applicant: NEMERA SZCZECIN SPOLKA Z OGRANICZONAODPOWIEDZIA-LNOSCIA, Szczecin (PL)

(72) Inventors: Adam Stefanski, Gniezno (PL); Alberto Lozano Platonoff, Szczecin (PL)

(73) Assignee: NEMERA SZCZECIN SPOLKA Z OGRANICZONAODPOWIEDZIA-LNOSCIA, Szczecin (PL)

( * ) Notice: Subject to any disclaimer, the term of this patent is extended or adjusted under 35 U.S.C. 154(b) by 416 days.

This patent is subject to a terminal disclaimer.

(21) Appl. No.: 17/346,784

(22) Filed: Jun. 14, 2021

(65) Prior Publication Data
US 2021/0307913 A1    Oct. 7, 2021

Related U.S. Application Data

(63) Continuation of application No. 16/315,580, filed as application No. PCT/EP2017/066317 on Jun. 30, 2017, now Pat. No. 11,052,194.

(30) Foreign Application Priority Data

Jul. 7, 2016    (EP) ..................... 16461534

(51) Int. Cl.
*A61M 5/20*     (2006.01)
*A61M 5/315*    (2006.01)
(Continued)

(52) U.S. Cl.
CPC .......... *A61M 5/20* (2013.01); *A61M 5/31525* (2013.01); *A61M 5/31553* (2013.01);
(Continued)

(58) Field of Classification Search
None
See application file for complete search history.

(56) References Cited

U.S. PATENT DOCUMENTS

| 533,575 A | 2/1895 | Wilkens |
| 2,444,570 A | 8/1946 | Lawrence et al. |
| (Continued) | | |

FOREIGN PATENT DOCUMENTS

| DE | 3609555 | 9/1987 |
| EP | 0295075 | 12/1991 |
| (Continued) | | |

*Primary Examiner* — Jenna Zhang
(74) *Attorney, Agent, or Firm* — Browdy and Neimark, PLLC

(57) ABSTRACT

An injection device for delivering equal doses of a fluid contained in a reservoir, the device having a housing, and an arming mechanism and a dose delivery mechanism arranged therein, the housing coupled to an enclosure for the reservoir. The arming mechanism includes an axially non-displaceable and rotatable setting sleeve. The setting sleeve is coupled with a spring strained by the rotation of the setting sleeve during arming of the device. The dose delivery mechanism includes a screw ring and a nonrotatable and axially displaceable piston rod within the setting sleeve. The piston rod cooperates with the screw ring so that during arming, the screw ring and the piston rod are immobilized, and during delivery of each dose the piston rod is displaced along the housing due to unwinding of the spring and rotation of the screw ring, the displacement of the piston rod causing the fluid to be discharged from the reservoir.

12 Claims, 10 Drawing Sheets

(51) Int. Cl.
  *A61M 5/32*    (2006.01)
  *A61M 5/34*    (2006.01)

(52) U.S. Cl.
  CPC ...... *A61M 5/3156* (2013.01); *A61M 5/31583* (2013.01); *A61M 5/3202* (2013.01); *A61M 5/347* (2013.01); *A61M 5/3155* (2013.01)

(56) References Cited

U.S. PATENT DOCUMENTS

| | | | |
|---|---|---|---|
| 2,717,597 | A | 12/1952 | Hein, Jr. |
| 4,470,317 | A | 9/1984 | Sabloewski et al. |
| 4,498,904 | A | 9/1985 | Turner et al. |
| 5,304,152 | A | 4/1994 | Sams et al. |
| 5,320,609 | A | 6/1994 | Haber et al. |
| 5,480,387 | A | 1/1996 | Gabriel et al. |
| 5,505,704 | A | 4/1996 | Pawelka |
| 5,626,566 | A | 5/1997 | Peterson |
| 5,674,204 | A | 10/1997 | Chanoch et al. |
| 5,688,251 | A | 11/1997 | Chanoch et al. |
| 6,083,197 | A | 7/2000 | Umbaugh |
| 6,221,046 | B1 | 4/2001 | Burroughs et al. |
| 6,899,698 | B2 | 5/2005 | Sams et al. |
| 7,896,850 | B2 | 3/2011 | Kronestedt |
| 7,918,833 | B2 | 3/2011 | Veasey |
| 8,357,120 | B2 | 1/2013 | Petersen |
| 8,376,993 | B2 | 2/2013 | Cox et al. |
| 8,512,297 | B2 | 8/2013 | Veasey |
| 8,603,044 | B2 | 12/2013 | Veasey |
| 8,608,708 | B2 | 12/2013 | Cowe |
| 8,617,109 | B2 | 12/2013 | Kronestedt et al. |
| 8,663,167 | B2 | 3/2014 | Bartha |
| 8,679,069 | B2 | 3/2014 | Veasey |
| 8,684,969 | B2 | 4/2014 | Moller |
| 8,915,889 | B2 | 12/2014 | Cox et al. |
| 8,920,383 | B2 | 12/2014 | Enggaard |
| 8,992,486 | B2 | 3/2015 | Veasey |
| 9,011,386 | B2 | 4/2015 | Kronestedt |
| 9,011,391 | B2 | 4/2015 | Veasey |
| 9,022,994 | B2 | 5/2015 | Moser |
| 9,044,548 | B2 | 6/2015 | Miller |
| 9,095,658 | B2 | 8/2015 | Wieselblad |
| 9,138,542 | B2 | 9/2015 | Smith |
| 9,205,195 | B2 | 12/2015 | Burren et al. |
| 9,233,211 | B2 | 1/2016 | Veasey |
| 9,408,979 | B2 | 8/2016 | Veasey |
| 9,415,165 | B2 | 8/2016 | Cowe |
| 9,526,844 | B2 | 12/2016 | Veasey |
| 9,561,333 | B2 | 2/2017 | Cox et al. |
| 9,566,386 | B2 | 2/2017 | Stefanski |
| 9,623,190 | B2 | 4/2017 | Veasey |
| 9,687,611 | B2 | 6/2017 | Moeller |
| 9,775,954 | B2 | 10/2017 | Veasey |
| 2002/0052578 | A1 | 5/2002 | Moller |
| 2004/0059299 | A1 | 5/2004 | Moller |
| 2006/0276753 | A1 | 12/2006 | Kronestedt |
| 2007/0129687 | A1 | 6/2007 | Marshall |
| 2009/0054851 | A1 | 2/2009 | Radmer |
| 2009/0227955 | A1 | 9/2009 | Hirschel |
| 2010/0010454 | A1* | 1/2010 | Marshall ............... A61M 5/326 604/208 |
| 2010/0298781 | A1 | 11/2010 | Hogdahl |
| 2011/0034878 | A1 | 2/2011 | Radmer |
| 2012/0283647 | A1 | 11/2012 | Cronenberg |
| 2014/0350484 | A1* | 11/2014 | Kohlbrenner ..... A61M 5/31583 604/222 |
| 2015/0080812 | A1 | 3/2015 | Enggaard |
| 2015/0148754 | A1* | 5/2015 | Eich ...................... A61M 5/20 604/235 |
| 2015/0265776 | A1 | 9/2015 | van der Beek |
| 2015/0290397 | A1 | 10/2015 | Wieselblad |
| 2015/0367078 | A1 | 12/2015 | Pedersen |
| 2016/0051770 | A1 | 2/2016 | Jones |
| 2016/0121052 | A1 | 5/2016 | Burren |
| 2016/0136358 | A1 | 5/2016 | Oakley |
| 2016/0151577 | A1 | 6/2016 | Newton |
| 2016/0158456 | A1* | 6/2016 | Oakley ............. A61M 5/31535 604/209 |
| 2016/0317752 | A1 | 11/2016 | Cowe |
| 2017/0087307 | A1 | 3/2017 | Cox |
| 2017/0100547 | A1 | 4/2017 | Stefanski |
| 2017/0119973 | A1 | 5/2017 | Roervig |
| 2017/0224924 | A1 | 8/2017 | Christensen |
| 2018/0221587 | A1* | 8/2018 | Keitel ............... A61M 5/31553 |

FOREIGN PATENT DOCUMENTS

| | | |
|---|---|---|
| EP | 0937471 | 9/2005 |
| EP | 1728529 | 7/2008 |
| EP | 1819382 | 10/2009 |
| EP | 1909870 | 3/2011 |
| EP | 2364742 | 9/2011 |
| EP | 1694387 | 7/2012 |
| EP | 2484395 | 8/2012 |
| EP | 1885414 | 11/2012 |
| EP | 2526987 | 11/2012 |
| EP | 1885415 | 5/2013 |
| EP | 2586477 | 5/2013 |
| EP | 2586478 | 5/2013 |
| EP | 1861141 | 12/2013 |
| EP | 2722931 | 4/2014 |
| EP | 2493533 | 2/2015 |
| EP | 2488232 | 1/2016 |
| EP | 2913075 | 5/2017 |
| WO | 1991/14467 | 10/1991 |
| WO | 1999/38554 | 8/1999 |
| WO | 2002053214 | 7/2002 |
| WO | 2006045526 | 5/2006 |
| WO | 2006126902 | 11/2006 |
| WO | 2007063342 | 6/2007 |
| WO | 2008087071 | 7/2008 |
| WO | 2015197629 | 12/2015 |
| WO | 2016/016184 | 2/2016 |
| WO | 2016/041883 | 3/2016 |
| WO | 2016107790 | 7/2016 |

* cited by examiner

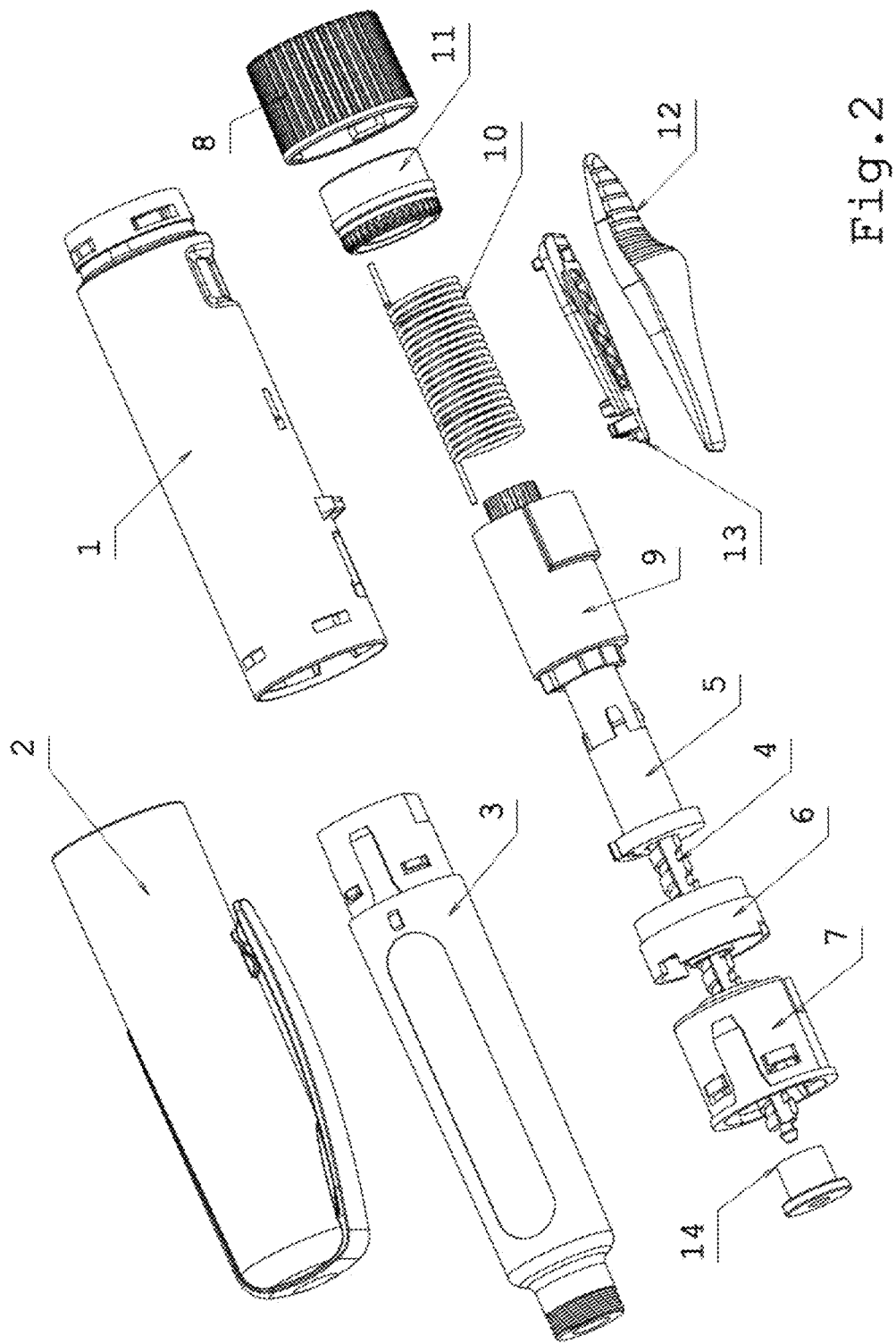

INJECTION DEVICE FOR DELIVERING A DEFINED NUMBER OF EQUAL DOSES OF A FLUID SUBSTANCE

The invention concerns the field of devices for delivering by injection a fluid substance, in particular a pharmaceutical substance, to a patient. The pharmaceutical substance may be any injectable pharmaceutical, e.g. insulin or growth hormone.

Specifically, the invention relates to an injection device for delivering a defined number of equal doses of a fluid substance.

Devices of the above described type for repeated injection of a fixed dose of a pharmaceutical substance are known; they may be driven by a helical pressure spring. Such devices are armed by rotation of a driving sleeve; the rotation causes the driving sleeve to be translated along the axis towards the proximal end and the driving spring to be simultaneously compressed. As a consequence of such construction, in order to prevent arming the device for delivery of a next dose after a number of doses have been delivered, further translation of the driving sleeve along the axis towards the proximal is blocked.

The terms "distal" and "proximal" are used here in relation to various elements and they should be understood as meaning respectively "the side of the end applied to a patient" and "the side of the end held by a user".

However, in the above described devices a helical pressure spring is used which does not enable the initial tension of the spring to be precisely set. This is caused by the fact that production spring height tolerance is relatively wide in comparison to the space occupied by the spring within the device. Consequently, the operational limits of the spring in such an injection device allow for only slight changes in its acting force.

It was an object of the present invention to provide an injection device for delivering a defined number of equal doses of a fluid substance in which a torsion spring is used. The advantage of such a spring is that its initial tension may be precisely set during the assembly of the injection device. The torsion spring is longer and hence it has a more uniform profile within the limits required for generating an injection.

According to the invention an injection device is provided for delivering a defined number of equal doses of a fluid substance contained in a reservoir, the device having a housing within which an arming mechanism and a dose delivery mechanism are arranged along the longitudinal axis of the housing, the housing being coupled to an enclosure adapted for receiving the reservoir with the fluid substance, the arming mechanism comprising a setting sleeve which is axially non-displaceable and rotatable around said axis of the housing in two opposite directions by a defined setting angle, the setting sleeve being coupled with a spring which is strained by the rotation of the setting sleeve during arming of the device; the dose delivery mechanism comprising a screw ring and a piston rod which is non-rotatable and axially displaceable within the setting sleeve, the piston rod cooperating with the screw ring so that during arming of the device the screw ring and the piston rod are immobilized, and during delivery of each dose the piston rod is displaced along the housing by a defined distance due to unwinding of the spring and rotation of the screw ring, the displacement of the piston rod causing the fluid substance to be discharged from the reservoir.

The injection device according to the invention is characterized in that the device is provided with blocking means preventing arming of the device for delivery of a subsequent dose after said defined number of doses of a fluid substance have been delivered, the blocking means comprising at least one longitudinal protrusion located near the distal end of the setting sleeve on its inside surface, and at least one longitudinal arm located at the proximal end of the piston rod, the at least one longitudinal protrusion and the at least one longitudinal arm mutually block each other after said defined number of doses of a fluid substance have been delivered which prevents rotation of the setting sleeve by the entire setting angle in the arming direction.

Preferably, the screw ring has an internal thread and the piston rod has an external thread, said threads cooperating during the rotation of the screw ring.

The spring is preferably mounted on the setting sleeve and the arming mechanism further comprises a scale having a form of a sleeve surrounding the setting sleeve and the spring, the distal ends of the spring and of the scale being coupled in rotation with the setting sleeve, the proximal end of the spring being secured to the housing.

The external surface of the piston rod preferably comprises at least one longitudinal groove and the dose delivery mechanism further comprises a blocking sleeve having at least one blocking projection and preventing the rotation of the piston rod by means of engagement of the at least one blocking projection with said at least one groove.

Preferably, the screw ring is selectively engaged in rotation with the setting sleeve by means of projections arranged on the internal surface of the screw ring in equal distances defined by the setting angle and of an elastic arm located on the distal end of the setting sleeve, the elastic arm engaging one of said projections after each rotation by the setting angle, the elasticity of the arm enabling further rotation of the setting sleeve by a next setting angle.

The screw ring and the piston rod are preferably immobilized during arming of the device by means of a trigger mechanism located on the housing.

Preferably, the trigger mechanism comprises a trigger engaged with the housing, the trigger being moveable between a first position in which it blocks the rotation of the screw ring and a second position in which the screw ring is free to rotate; the trigger mechanism further comprising a trigger slide which is displaceable along the housing and coupled with the trigger.

The trigger preferably comprises an elastic element enabling an automatic return of the trigger and the trigger slide to the first position in which the screw ring is blocked.

The trigger preferably comprises a projection which in the first position of the trigger, with the screw ring blocked, is engaged with a corresponding recess of the screw ring.

Preferably, the projection engages the recess with a play.

An embodiment of the subject of the invention is shown in the appended drawings in which:

FIG. 2 shows an exploded perspective view of the injection device according to the invention;

Figure 1:
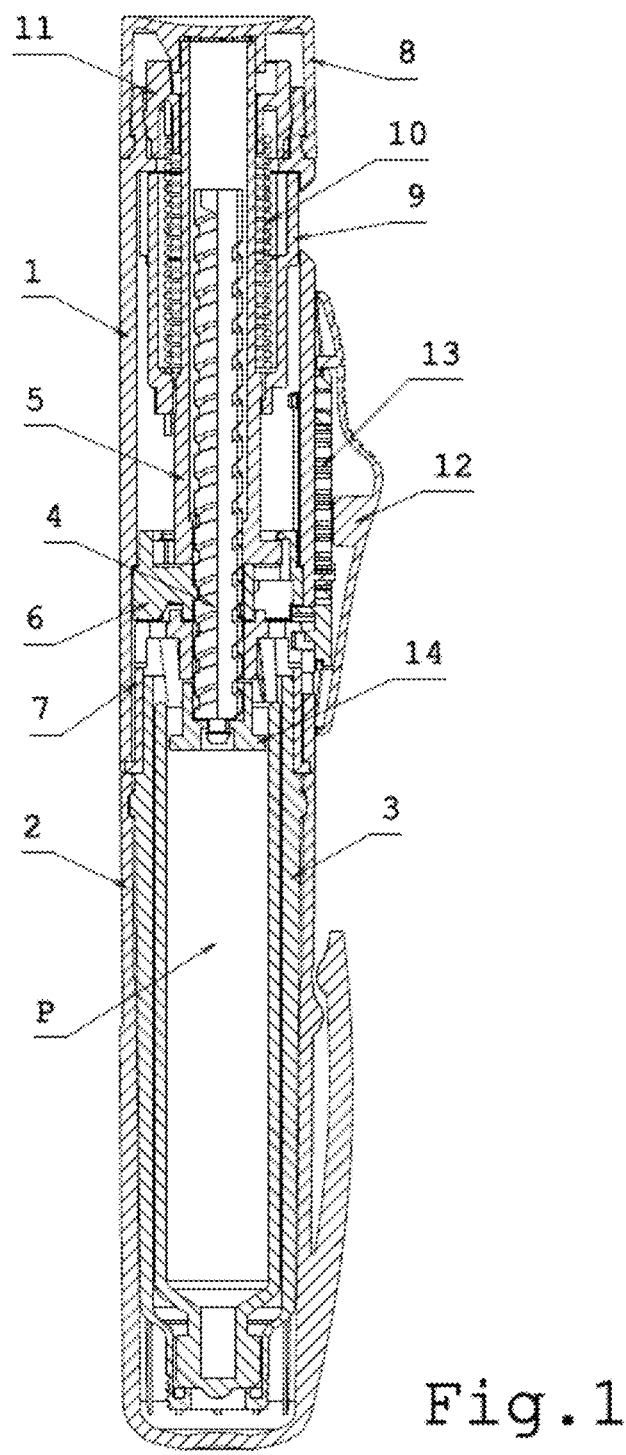
FIG. 1 shows a longitudinal cross-section of an injection device according to the invention.

In FIG. 1, the injection device is shown in a longitudinal cross-section, in a ready for use state, before the first use. As may be seen, mechanisms of the device and an enclosure 3 with a fluid substance reservoir P are located within a housing 1 coupled to a cap 2. A piston rod 4 is used for discharging consecutive doses of the substance from the reservoir. The piston rod 4 cooperates with a setting sleeve 5, a screw ring 6 and a blocking sleeve 7. The device is being armed for delivery of consecutive doses of the substance by means of a knob 8 engaged with a scale 9. Rotation of the knob causes straining of a torsion driving spring 10. The spring 10 is immobilized in the housing 1 by a lock member 11. A trigger mechanism comprising a trigger slide 12 and a trigger 13 is arranged on the outside of the housing 1.

FIG. 2 shows the injection device according to the invention in an exploded view. The setting sleeve 5, the spring 10 and the scale 9 form together the arming mechanism operated by the knob 8. On the other hand, the piston rod 4, the screw ring 6 and the blocking sleeve 7 form together the dose 3s delivery mechanism.

The arming mechanism and the dose delivery mechanism are arranged one after the other along the longitudinal axis of the device as seen from its proximal end. The enclosure 3 containing the reservoir P with a fluid substance is coupled to the housing 1 downstream the dose delivery mechanism.

Below, the arming mechanism will be described. The setting sleeve 5 is mounted on the un-rotatable piston rod 4 that can be displaced within the setting sleeve 5 only in the distal direction. The setting sleeve is surrounded by the driving spring 10 over which the scale 9 having a form of sleeve is mounted. Rotation of the setting sleeve 5 is realized by means of the knob 8.

Figure 3A:
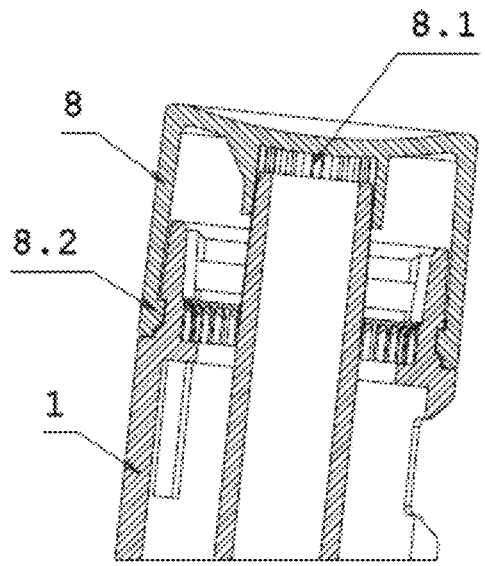
FIGS. 3a, 3b, 3c show three partially sectional views of a knob and the coupling of a spring with a housing of the device.

FIG. 3a shows in detail the knob 8 and the way it is coupled to the setting sleeve 5 and the housing 1. The knob 8 is coupled to the setting sleeve 5 by means of multiple locking projections 8.1 allowing to transfer rotational movement. The knob 8 is coupled to the housing 1 by detents 8.2 enabling rotation of the knob 8 relative to the housing 1. The lock member 11 of the spring 10 is located between the knob 8 and the housing 1 (FIGS. 3b and 3c).

Figure 3C:
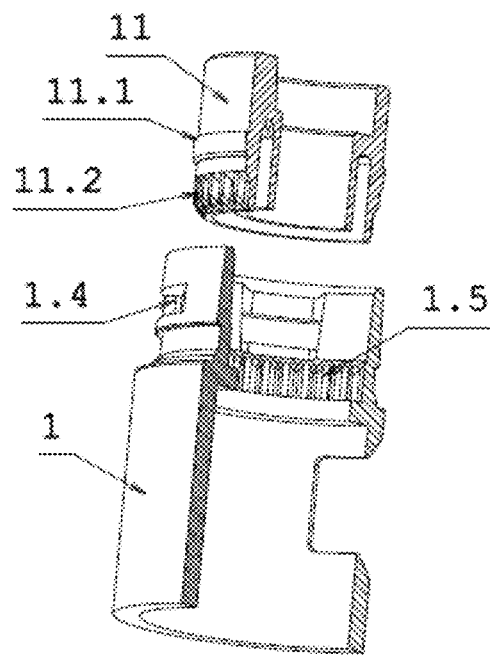
Figure 3B:
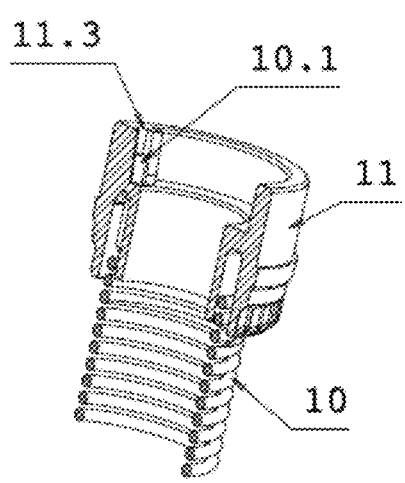

FIG. 3b shows how a proximal end 10.1 of the driving spring 10 is secured during the assembly of the device in an opening 11.3 of the lock member 11. Upon fixing the initial tension of the spring, the lock member 11 is being permanently secured to the housing 1 after which these two elements may not be disassembled.

As shown in FIG. 3c the lock member 11 has a protrusion 11.1 for securing the lock member 11 to the housing that is equipped with corresponding detents 1.4. Before assembly, the initial tension of the spring 10 is being set by way of rotating the lock member 11 by a necessary angle. A toothed flange 11.2 located at a distal end of the lock member 11 engages a toothed flange 1.5 provided on the housing, and permanently secures the position of the lock member 11 rotated by an angle necessary to maintain the initial tension of the spring 10.

Figure 4A:
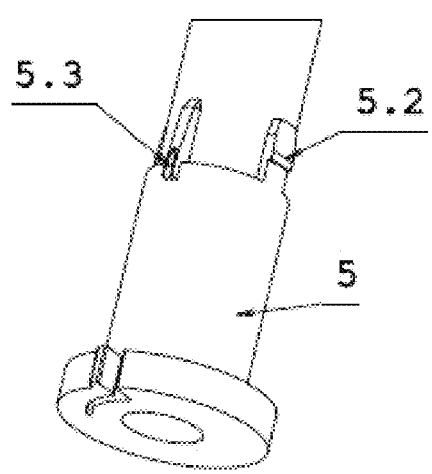
FIGS. 4a, 4b, 4c, 4d show four partially sectional views of the coupling of a setting sleeve with a scale and of the spring with the housing.
Figure 4B:
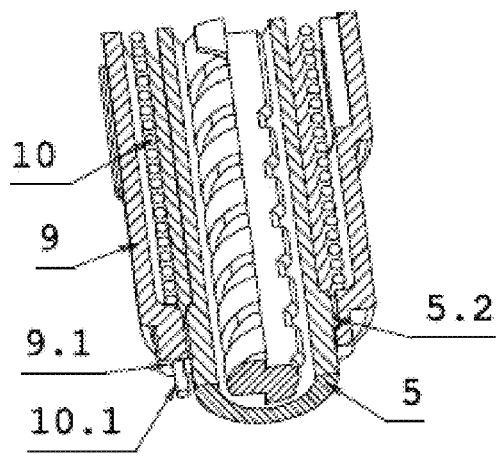
Figure 4C:
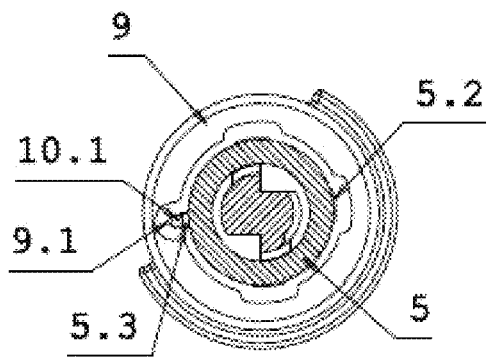
Figure 4D:
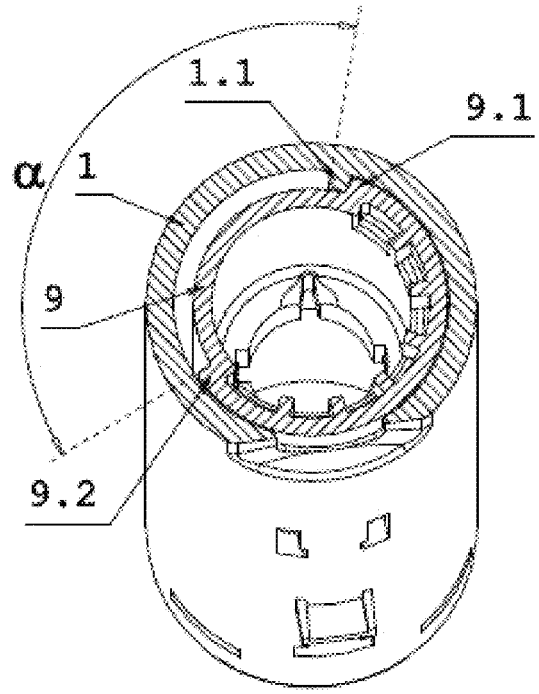

FIGS. 4a, 4b, 4c, 4d show the way of coupling of the setting sleeve 5 with the scale 9 and the spring 10, as well as of the scale 9 with the housing 1. The connection of the setting sleeve 5 with the scale 9 is a latch connection in order to promote precise positioning of these elements relative to each other. The setting sleeve 5 is provided with projections 5.2 on its periphery (FIG. 4a) for coupling with the scale 9 and a projection 5.3 for securing the spring 10 in order to prevent their accidental disassembly during the assembly of the device and the setting of the initial tension of the spring 10. The spring 10 is secured in a dedicated slot 9.1 of the scale 9 (FIGS. 4b and 4c). The slot 9.1 is shaped in such a way that a bent end 10.1 of the spring, upon being secured in the scale 9, is pressed by the projection 5.3 of the setting sleeve 5. This arrangement causes the end 10.1 of the spring to be pressed deeper into the converging slot 9.1 of the scale 9 which in turn results in generating a static friction force big enough to prevent accidental disassembly. As can be seen in FIG. 4d, the scale 9 mounted in the housing 1 has a determined position and it may be rotated within the housing 1 to an extent defined by the projections 9.2 abutting a rib 1.1 extending axially along the housing 1. The mutual position of these elements defines the operational limits of the injection device. Between the projections 9.2 a printed part of the scale is located comprising indications visible by a window in the housing 1.

Figure 5A:
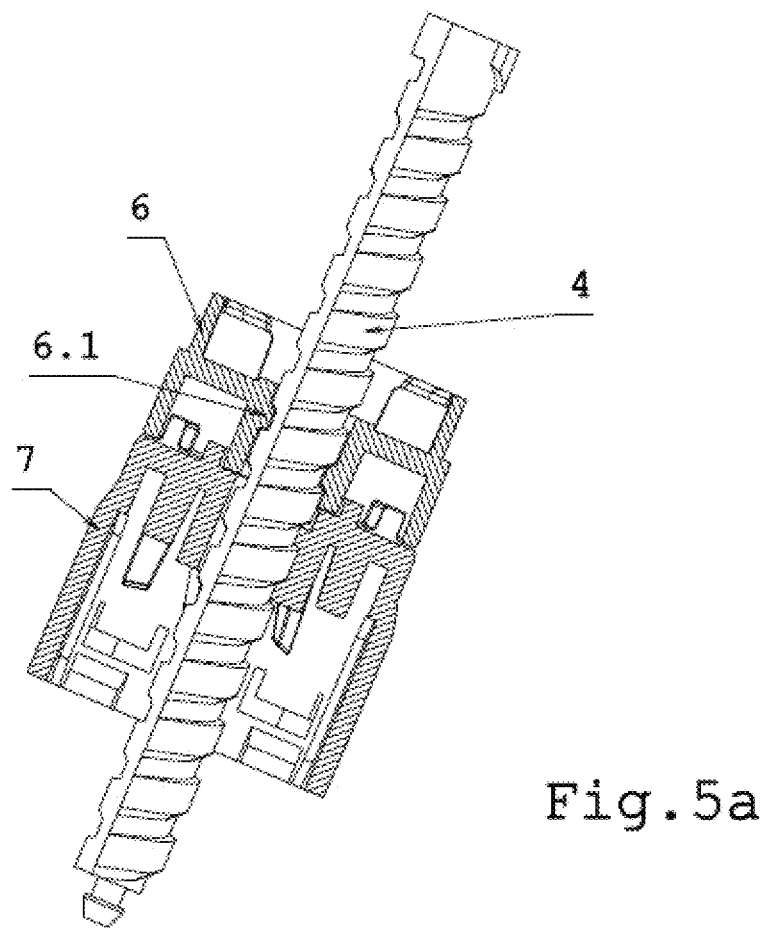
FIGS. 5a, 5b show two partially sectional views of a fragment of a dose delivery mechanism.
Figure 5B:
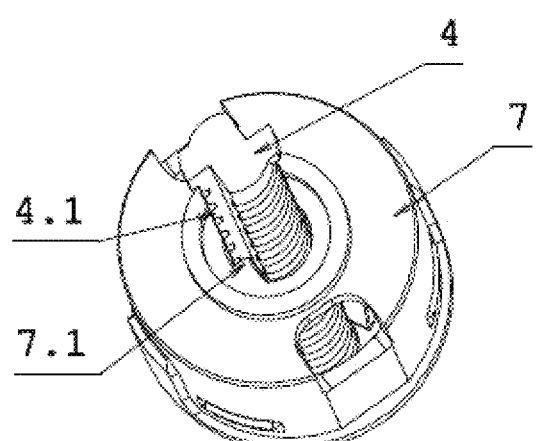

The dose delivery mechanism is shown in detail in FIGS. 5a-5b and 6a-6c. FIG. 5a shows a longitudinal cross-section of a part of the injection device comprising the piston rod 4, the screw ring 6 and the blocking sleeve 7. As shown in FIG. 5a, the piston rod 4 having an external thread 4.0 is engaged with the screw ring 6 via its internal thread 6.1. The thread 6.1 is selected according to the required dose of a substance to be discharged as a consequence of rotation of the screw ring 6 by a defined angle $\alpha$. The dose may be set as e.g. 80 microliters corresponding to a rotation by an angle $\alpha$ 120°. FIG. 5b shows that the piston rod 4 has a non-circular cross-section with two longitudinal grooves 4.1 extending along its external surface. The grooves 4.1 engage with corresponding ribs 7.1 of the blocking sleeve 7. In the described embodiment there are two grooves 4.1 and two ribs 7.1, but there may be at least one groove and at least one rib or more. As a consequence, the piston rod 4 is blocked against rotation in the blocking sleeve 7 and is being displaced axially by a defined distance when the screw ring 6 is rotated.

Figure 6A:
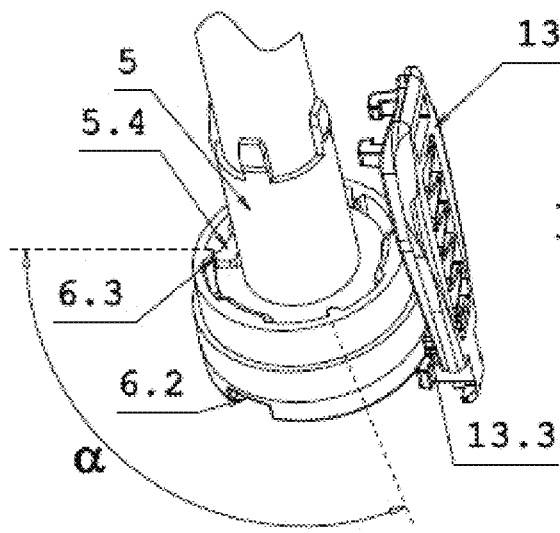
FIGS. 6a, 6b, 6c show three partially sectional views of another fragment of the dose delivery mechanism.
Figure 6B:
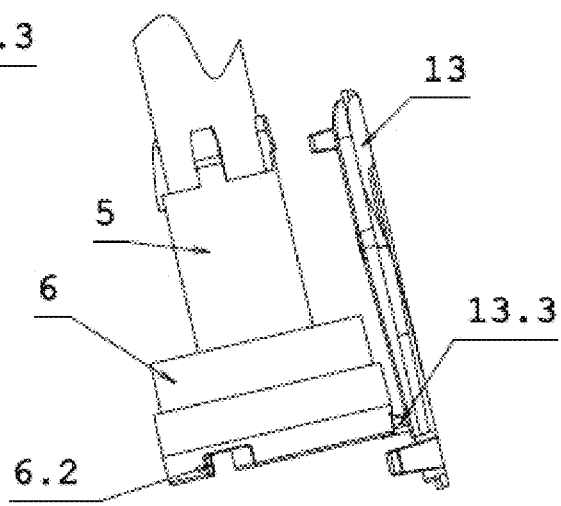
Figure 6C:
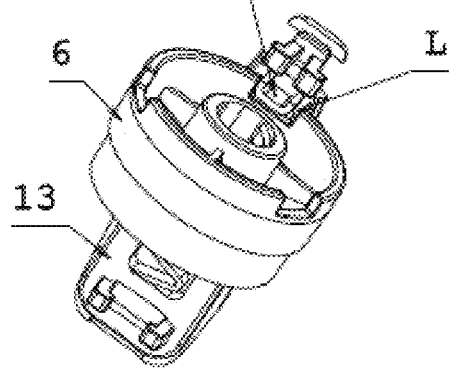
Figure 7A:
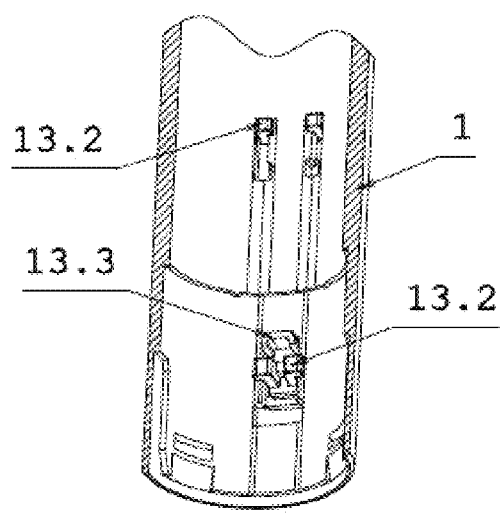
FIGS. 7a, 7b, 7c show three partially sectional views of a trigger mechanism of the injection device according to the invention.
Figure 7B:
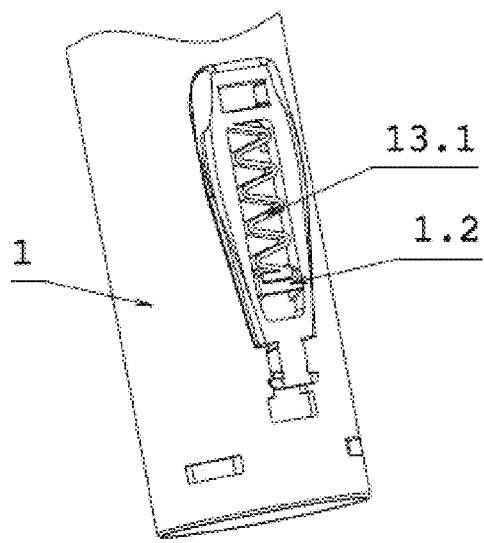
Figure 7C:
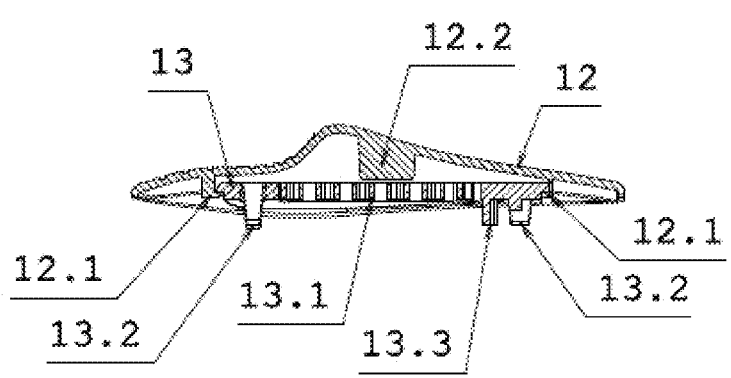

FIGS. 6a-6c present the way of cooperation of the setting sleeve 5 with the screw ring 6 and the trigger 13 constituting a part of the trigger mechanism described in relation to FIGS. 7a-7c.

Figure 8A:
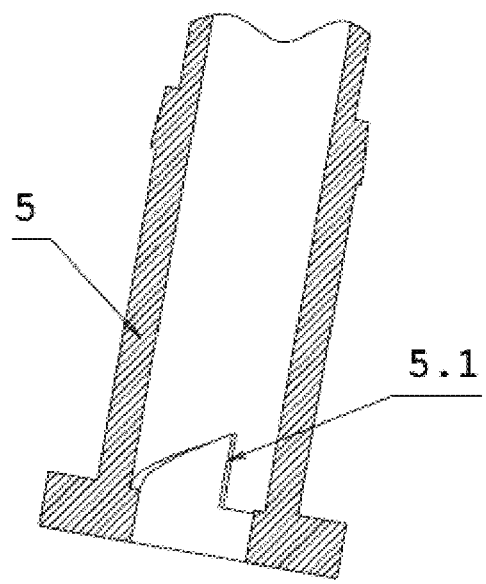
FIGS. 8a and 8b show two views of means preventing arming the device for delivery of a subsequent dose.
Figure 8B:
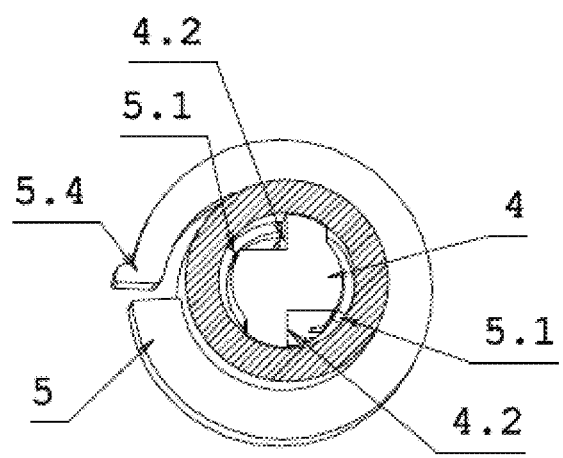

As can be seen in FIG. 6a, the setting sleeve 5 has at its distal end an elastic arm 5.4 extending peripherally (best shown in FIG. 8b). During arming of the device for delivery of a dose, i.e. during the rotation of the setting sleeve 5 by a setting angle $\alpha$ which causes the driving spring 10 to be strained, the elastic arm 5.4 catches succeeding projections 6.3 provided on the inside periphery of the screw ring 6. During the arming, the screw ring 6 is blocked against rotation by means of the trigger 13 which is secured within the housing 1. As shown in FIG. 6.2, the trigger 13 has a projection 13.3 engaging corresponding recesses 6.2 of the screw ring. The number of the recesses 6.2 is selected according to the angle $\alpha$ by which the screw ring 6 is rotated in order to discharge the dose, i.e. to the size of the dose.

Upon release of the trigger 13, the screw ring 6 is free to rotate around its axis so it may take over the rotation of the setting sleeve 5. The setting sleeve 5 is pushed by the unwinding spring 10 which was strained during the arming of the device when the screw ring 6 was blocked against rotation.

As shown in FIG. 6c, a certain play L exists between the trigger 13 and the screw ring 6 in their engaged position (the recesses 6.2 are slightly larger than the projections 13.3 of the trigger 13). The function of the play L is to enable qualifying of a dose after the device was armed and prior the delivery of the dose, i.e. enable filling the cannula of a newly mounted injection needle with the fluid so that the cannula does not contain air and the dose is more precise. Due to this arrangement priming of the device is not necessary before delivery of the dose. Hence, directly after arming of the device and before releasing of the trigger 13, both the setting sleeve 5 and the screw ring 6 undergo a priming rotation within the limits of the play L, causing the piston rod 4 to be slightly displaced in the distal direction. Only upon release of the trigger 13 is the rotational energy, accumulated in the spring 10 during the arming, transferred to the screw ring 6 from the setting sleeve 5.

In FIGS. 7a, 7b and 7c the trigger mechanism of the device according to the invention is shown in three views. FIG. 7a shows a fragment of the inside of the housing 1. The trigger 13 is secured to the housing 1 by means of hooks 13.2 that allow axial translation of the trigger 13 in order to disengage it from the screw ring 6. When all the parts of the device have been assembled, the trigger 13 is blocked against excessive dislocation (best seen in FIG. 1) so that it may not be dismounted. In FIG. 7b an elastic element 13.1 of the trigger 13 is shown. Upon the delivery of a dose of the pharmaceutical substance, the elastic element 13.1 causes the trigger 13 to return to its position of engagement with the screw ring 6. The elastic element 13.1 cooperates with the housing via a catch 1.2. FIG. 7c is a longitudinal cross-section of the trigger mechanism showing that the trigger slide 12 is coupled to the trigger 13 by means of hooks 12.1. Additionally, the trigger slide 12 has a rib 12.2 preventing the elastic element 13.1 of the trigger 13 from being accidentally dismounted from the housing 1 during the use of the device.

The injection device according to the invention is equipped with blocking means preventing arming of the device for delivery of a subsequent dose after a defined number n of doses of a fluid substance have been delivered. The blocking means will be described below with reference to FIGS. 8a-8b.

FIG. 8a presents a fragment of the setting sleeve 5 showing its inside. As can be seen, the setting sleeve 5 is provided on its inside surface near the distal end with two longitudinal protrusions 5.1. FIG. 8b shows that the proximal end of the piston rod 4 has two longitudinal arms 4.2. The longitudinal protrusions 5.1 and the arms 4.2 come to mutual engagement after delivery of n doses of a fluid substance which makes it impossible to rotate the setting sleeve 5 by a full setting angle α in the arming direction.

The protrusions 5.1 and the arms 4.2 may have various shapes. Furthermore, an embodiment is envisageable in which the setting sleeve 5 has just one protrusion 5.1 and the piston rod 4 has just one arm 4.2. In the described embodiment the two opposed protrusions 5.1 of the setting sleeve 5 have a shape as shown in FIG. 8a (only one protrusion 5.1 is visible in the figure). The piston rod 4 may only be displaced axially and the setting sleeve 5 may only be rotated. Hence, after the last full dose has been delivered, the end of the piston rod 4 comes to the engagement with the protrusions 5.1 of the setting sleeve 5 preventing its rotation by a full setting angle α which is required to arm the device for delivery of a next dose of the substance. In this situation the setting sleeve 5 may only be rotated by a part of the angle α but this is not enough for the elastic arm 5.4 to catch a succeeding projection 6.3 in order to arm the device. After an unsuccessful attempt to arm the device for delivery of a dose outside the operational limits, the setting sleeve 5 returns to its initial position, which is visible on the scale.

The injection device is supplied to a recipient in a semi-assembled state. Therefore, it is essential to ensure that the individual elements are properly coupled so that the mechanisms may not be disassembled and—after addition of the enclosure with the fluid substance reservoir by the producer—that the complete device may not be dismantled.

In FIGS. 9a, 9b, 9c, 9d and 9e means for coupling individual elements of the device are shown. These means include among others the latches 7.2 located on the blocking sleeve 7, visible in FIG. 9a, that come to engagement with corresponding recesses 1.3 of the housing 1 and the latches 3.1 located on the enclosure 3 of the reservoir, visible in FIG. 9b, that come to engagement with recesses 7.3 of the blocking sleeve 7. Such connection ensures that the device may not be dismantled without damaging its essential elements which would result in making it impossible to reassemble the device. Additionally, it should be noted that also after a defined number n of the doses have been delivered it is impossible to reset the piston rod 4 in its initial position without disassembling the whole device, which further guarantees the single-use feature (including delivery of n doses) of the injection device.

Figure 9A:
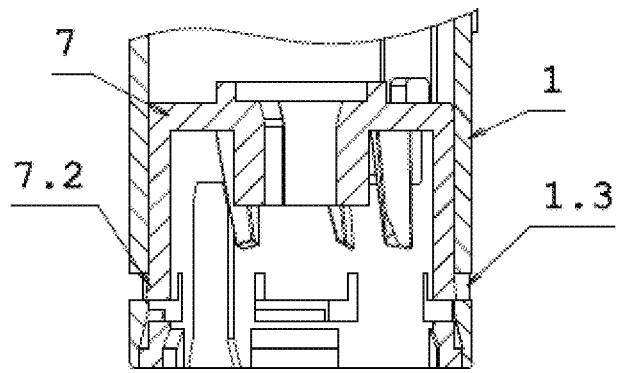
FIGS. 9a, 9b, 9c, 9d, 9e show cross-sections of different parts of the device comprising means enabling correct coupling of individual elements of the device.
Figure 9B:
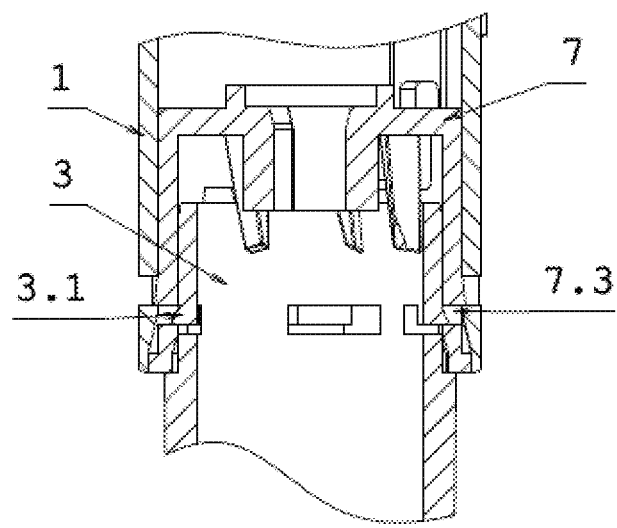
Figure 9C:
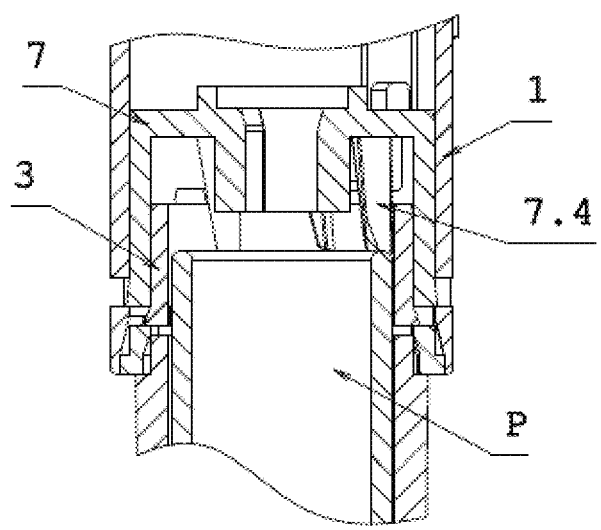

Moreover, as shown in FIG. 9c, the blocking sleeve 7 is provided with inside elastic arms 7.4 for correct positioning of the reservoir P during the assembly of the injection device. The arms 7.4 are asymmetric and designed in such a way that they are being bent in one direction during the assembly so as to press the reservoir P and compensate for its possible length difference.

Figure 9D:
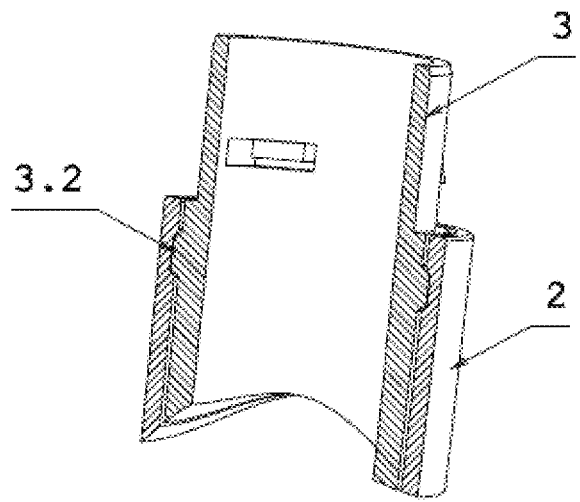
Figure 9E:
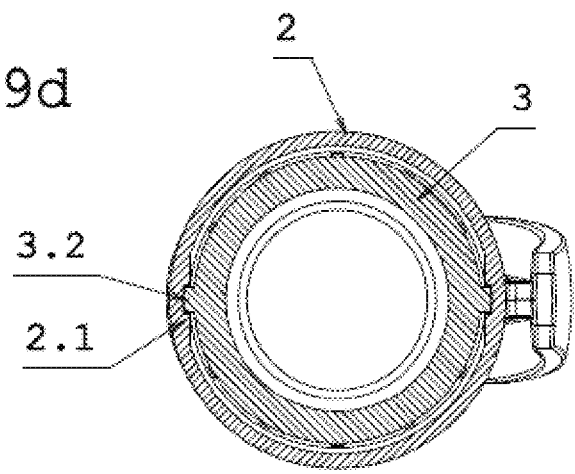

FIG. 9d shows how the reservoir enclosure 3 is coupled to the cap 2 by means of a projection 3.2 enabling mutual connection of these two elements in any angular position.

On the inside periphery of the cap 2 there are additional catches 2.1 (FIG. 9e) so that when the cap 2 is mounted on the reservoir enclosure 3, it may be set in exactly two angular positions by turning it in any direction so that the orientation of the clip of the cap relative to the rest of the device is constant.

The design of the cap 2 (FIG. 1) is such that an injection needle may not be fitted inside it when mounted on the device in order to force the user to change the needle before each use.

Figure 10:
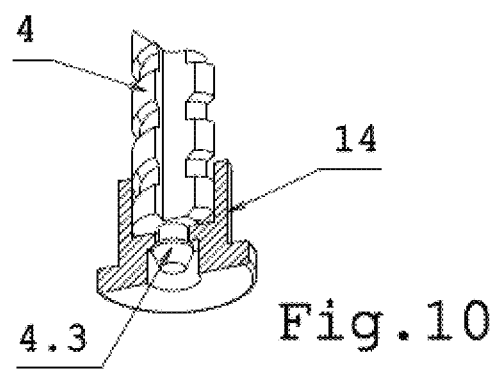
FIG. 10 shows a longitudinal cross-section of the distal end of a piston rod.

As shown in FIG. 10, presenting a longitudinal cross-section of the distal end of the piston rod 4, an ending 14 is fitted on the piston rod 4 by means of a catch 4.3, the function of the ending 14 being to increase the contact surface between the piston rod 4 and a plunger of the reservoir P with a fluid substance.

The invention claimed is:

1. An injection device for delivering of a defined number of equal doses of a fluid substance contained in a reservoir, the device having a housing within which an arming mechanism and a dose delivery mechanism are arranged along a longitudinal axis of the housing, the housing being coupled to an enclosure adapted for receiving the reservoir with the fluid substance, wherein the arming mechanism comprises rotatable setting sleeve, the setting sleeve being coupled to a spring, the dose delivery mechanism comprises a screw ring having an internal thread, a piston rod having an external thread and a non-circular cross-section, and a blocking sleeve engaged with the piston rod to prevent rotation of the piston rod, wherein the device further comprises a rotatable knob which is coupled to the setting sleeve in a way allowing to transfer rotational movement and an axially displaceable trigger, wherein the device is being armed for delivery of doses of the substance by rotation of the knob, wherein during arming of the device, the screw ring and the axial displaceable trigger are in an engaged position so that the screw ring is immobilized, during delivery of each dose, the axial displaceable trigger is released allowing rotation of the screw ring and displacement of the piston rod along the housing by a defined distance due to unwinding of the spring, the displacement of the piston rod causing the fluid substance to be discharged from the reservoir, wherein a certain play L exists between the axial displaceable trigger and the screw ring in the engaged position so that after arming of the device and before releasing of the axial displaceable trigger, both the setting sleeve and the screw ring undergo a priming rotation with the limits of said play L.

2. The injection device according to claim 1, wherein the spring is immobilized in the housing by a lock member secured to the housing.

3. The injection device according to claim 2, wherein the lock member is secured to the housing by cooperating protrusion and detent.

4. The injection device according to claim 2, wherein the lock member comprises a toothed flange engaging a toothed flange of the housing.

5. The injection device according to claim 1, wherein the setting sleeve comprises projection to secure the spring.

6. The injection device according to claim 1, wherein the setting sleeve is connected with the scale by the latch connection.

7. The injection device according to claim 1, wherein the axial displaceable trigger comprises a projection configured to engage the recesses in the screw ring.

8. The injection device according to claim 7, wherein number of recesses is selected according to an angle α.

9. The injection device according to claim 1, wherein the injection device comprises an elastic element causing the axial displaceable trigger to return to an initial position of engagement with the screw ring upon the delivery of a dose.

10. The injection device according to claim 1, wherein the injection device is equipped with blocking means preventing arming of the device for delivery of a subsequent dose after a defined number n of doses of a fluid substance have been delivered.

11. The injection device according to claim 1, wherein the blocking sleeve is provided with elastic arms.

12. The injection device according to claim 1, wherein the device may not be dismantled without damaging essential elements of the device that would make reassembling the device impossible.

* * * * *